(12) United States Patent
Graham

(10) Patent No.: US 7,033,398 B2
(45) Date of Patent: Apr. 25, 2006

(54) SINUS TARSI IMPLANT

(76) Inventor: Michael E. Graham, 45700 Schoenherr Rd., Shelby Township, MI (US) 48315

( * ) Notice: Subject to any disclaimer, the term of this patent is extended or adjusted under 35 U.S.C. 154(b) by 125 days.

(21) Appl. No.: 10/780,872

(22) Filed: Feb. 19, 2004

(65) Prior Publication Data

US 2005/0187636 A1    Aug. 25, 2005

(51) Int. Cl.
*A61F 2/42* (2006.01)
(52) U.S. Cl. .................. 623/21.18; 606/73
(58) Field of Classification Search ........... 623/47–49, 623/53, 55, 21.18; 606/73
See application file for complete search history.

(56) References Cited

U.S. PATENT DOCUMENTS

| | | | |
|---|---|---|---|
| 4,450,591 A * | 5/1984 | Rappaport .................. 128/898 |
| 5,057,109 A * | 10/1991 | Olerud ........................ 606/61 |
| 5,300,076 A * | 4/1994 | Leriche ........................ 606/73 |
| 5,360,450 A * | 11/1994 | Giannini .................. 623/21.19 |
| 6,053,920 A * | 4/2000 | Carlsson et al. .............. 606/72 |
| 6,136,032 A | 10/2000 | Viladot Perice et al. |
| 6,168,631 B1 | 1/2001 | Maxwell et al. |
| 6,443,954 B1 * | 9/2002 | Bramlet et al. ............... 606/62 |
| 6,607,535 B1 * | 8/2003 | Chan ........................... 606/95 |
| 2005/0177165 A1 * | 8/2005 | Zang et al. .................... 606/73 |
| 2005/0177243 A1 * | 8/2005 | Lepow et al. ............. 623/21.11 |

OTHER PUBLICATIONS

Dockery et al., "The Maxwell-Brancheau Arthroereisi (MBA) Implant . . . ," Foot and Ankle Quarterly. Winter 1999, vol. 12, No. 4, pp. 107-120.
Stagni et al., "Role of Passive Structures in the Mobility and Stability of the Human Subtalar Joint . . ." Foot & Ankle International. May 2003, vol. 24, No. 5, pp. 402-409.
MBA Subtalar Implant, Product Brochure, Kinetikos Medical Inc., Undated, 6 pages.

* cited by examiner

*Primary Examiner*—Bruce Snow
*Assistant Examiner*—Cheryl Miller
(74) *Attorney, Agent, or Firm*—Scott Houtteman; Kile Goekjian Reed & McManus (57) ABSTRACT

An arthroeresis-prosthesis (endorthosis) system comprising a sinus tarsi implant for the purpose of blocking abnormal motion between the talus and calcaneus while allowing normal motion and alignment. In a preferred embodiment, the prosthetic device is composed of a non-metallic, specialized medical grade polymer (polyetheretherketone-PEEK) that is a combination of a frustum of a right cine and an axially extending cylinder that is cannulated and partially structured on the exterior surface.

19 Claims, 4 Drawing Sheets

SINUS TARSI IMPLANT

BACKGROUND OF THE INVENTION

This invention relates to a medical apparatus for enhancing and for correcting skeletal mechanics. More specifically, this invention relates to the correction of certain bone alignment deformities that impair optimal biped mechanics.

Excessive pronation (hyperpronation) is caused by abnormal motion between two bones of the foot; the ankle bone (talus) and the heel bone (calcaneus). This abnormal motion will eventually lead to anatomical mal-alignment both proximally and distally. The abnormal motion is due to obliteration or closure of a naturally occurring space (sinus) formed between the talus and calcaneus.

This sinus is referred to anatomically as the sinus tarsi. In anatomical terms, the sinus tarsi is located anterior to the subtalar joint and posterior to the talocalcaneo-navicular joint. As will be described in greater detail below, the subtalar joint is formed by the posterior talar facet of the calcaneus and the posterior calcaneal facet of the talus. The talocalcaneonavicular joint is formed by the middle and anterior calcaneal facet of the talus and middle and anterior talar facet of the calcaneus.

Generally speaking, when a human biped is walking or running, the individual's talus acts as a "torque converter" to transfer the weight of the body to the foot. This weight transfer is accomplished via the motion of the subtalar joint, which is mainly movement of the talus onto the calcaneus. The normal mechanics of the subtalar joint produces a triplanar motion-motion through all three anatomical planes. This motion consists of supination, and pronation. Pronation occurs when the talus moves medially (inward), anterior (forward) and plantarly (inferiorly). Supination occurs when the talus moves laterally (outward), posteriorly (backward) and dorsally (upward). Normally, there should be approximately a two-to-one ratio of supination to pronation.

Some individuals suffer as a result of abnormal motion of the subtalar joint. This is often referred to as excessive pronation or, more specifically, hyperpronation. The pathomechanics of hyperpronation leads to significant deleterious effects to the bony architecture of the talus and calcaneus both proximally and distally. Hyperpronation is defined by excessive talar deviation medially (inward), anteriorly (forward), and plantarly (inferiorly).

Hyperpronation is detected and diagnosed through physical examination of the foot, both non-weight bearing and weight bearing examination, as well as radiographic evaluation of the foot. Non-weight bearing examination of hyperpronation is achieved by applying pressure to the fifth metatarsal head region of the foot to dorsiflex the foot (push the foot toward the front of the shin) and if the foot turns out-ward hyperpronation is present. In the weight-bearing examination, the person stands on his/her feet and the examiner observes both pronation and supination of the subtalar joint. Normally the foot should be in a "neutral" position, that is, neither pronated nor supinated. If the foot is in a pronated position while full weight is on the foot, the foot is considered hyperpronated.

Radiographic evaluation of hyperpronation is seen by examining the weight-bearing anterior-posterior (top to bottom) view and the lateral (side) view. These two projections show the relationship of the talus to the other foot bones. If the talus is medially (inward) and/or anteriorly (forward) deviated and/or plantarflexed (inferiorly) displaced hyperpronation is present.

Previous implants have been designed for insertion into the sinus tarsi in an attempt to treat foot disorders. In this, one envisioned design included a mushroom-shaped implant with a stem protruding from the bottom. The implant was held in place by inserting the stem into a hole drilled into the dorsum of the calcaneus. Unfortunately, drilling can weaken the calcaneus and often resulted in direct or ultimate fracture. Moreover, the stem of the implant is subject to fracture which, of course, again leads to failure of the procedure. Also, the surgical procedures necessary for implantation is somewhat and subject to physician error.

In another previously known design, an implant is threaded on an outer surface and screwed into the sinus tarsi. This implant is usually composed of high molecular weight polyethylene. Unfortunately, this device can only be gas sterilized. This allowed the device to deform under the compressive pressure to which it is subjected under normal post-operative condition. Furthermore, it was difficult to accurately locate the device properly within the sinus tarsi.

In yet another design, a cylindrical implant made of a titanium alloy is threaded on an outer surface. However, this implant only corrects one portion of the deformity while both the lateral and medial portions of the sinus tarsi need correction. Furthermore, a titanium implant is much harder than surrounding bone matter. This can lead to bone wear and/or deformation. In addition, fluoroscopy is required in order to verify the position which exposes a patient to radiation. The procedure for insertion requires two separate incisions on the medial and lateral aspect of the foot and calls for a below-the-knee cast for two weeks post-operatively. Finally, the implant is made available in a series of sizes. These implants vary in size, one from the next, by specific increments. Gaps in this series can lead to under and over correction.

The problems suggested in the preceding are not intended to be exhaustive but rather are among many which may tend to reduce the effectiveness of sinus tarsi implants known in the past. Other noteworthy problems may also exist; however, those presented above should be sufficient to demonstrate that previously known sinus tarsi implants will admit to worthwhile improvement.

OBJECTS OF THE INVENTION

It is a general object of the invention to obviate limitations in correcting abnormal foot mechanics of the type previously described.

An object of the invention is to insure proper foot motion by stabilizing the motion between the talus and calcaneus.

It is a related object of the invention to insure that both the medial and lateral aspects of these bones are stabilized.

Another object of the invention is to block hyperpronation between the talus and calcaneus while allowing normal foot motion.

A further object of this invention is to correct malalignment, both proximally and distally, of the talus and calcaneus.

Another object of the invention is to provide an implant that will not, over time, wear or deform the talus and calcaneus.

Still another object of the invention is to provide an implant that will not wear or deform over time and thus fail.

Another object is to provide an implant that will remain in place without a separate anchoring procedure.

Another object of the invention is a method of correctly positioning an implant in the space between the talus and calcaneus bones without having to verify the correct position with a fluoroscope and thus expose the user to radiation.

A further object of the invention is to provide less invasive surgery for inserting an implant.

A related object of the invention it to provide a sinus tarsi implant without requiring a post-operative below-the-knee cast.

BRIEF SUMMARY OF THE INVENTION

An embodiment of the present invention that is intended to accomplish at least some of the foregoing objects comprises blocking motion of the subtalar joint with an internally placed orthotic device. In medical terms, this embodiment comprises a subtalar arthroeresis endorthosis implantation system. The implant is termed a subtalar or, more specifically, a sinus tarsi arthroeresis which maintains the sinus tarsi in an anatomically correct alignment, allowing the normal physiological motion to occur while minimizing a tendency for abnormal pre-operative motion.

The sinus tarsi implant of the subject invention is generally funnel shaped or tapered and fits into the sinus tarsi. The implant comprises a frustum of a right cone portion as well as an integral extension. The frustum portion is considered the superficial or lateral portion of the implant and may be operably positioned within the lateral or sinus region of the sinus tarsi. A small diameter cylindrical portion of the implant is considered the medial side of the implant and will be operably positioned within a deeper side of the sinus tarsi, the canalis tarsi.

The surface of the implant optionally contains channels or a roughened texture in selected regions. These surface regions will, in a preferred embodiment, interact with the surrounding tissue. This interaction increases the mechanical retention between the surface of implant and the surrounding tissue and thus helps maintain the implant in a proper anatomical position.

The sinus tarsi implant of the subject invention is preferably constructed of a medical grade polymer. The polymer composition will allow for less trauma to the external bone surface as compared to a metal alloy based implant. The implant optionally has a hole bored through its longitudinal axis (a cannula) that allows for accurate placement into the sinus tarsi via a guide wire or guide peg.

BRIEF DESCRIPTION OF THE DRAWINGS

Other objects and advantages of the present invention will become apparent from the following detailed description of preferred embodiments taken in conjunction with the accompanying drawings wherein.

DETAILED DESCRIPTION OF THE INVENTION

Figure 1:
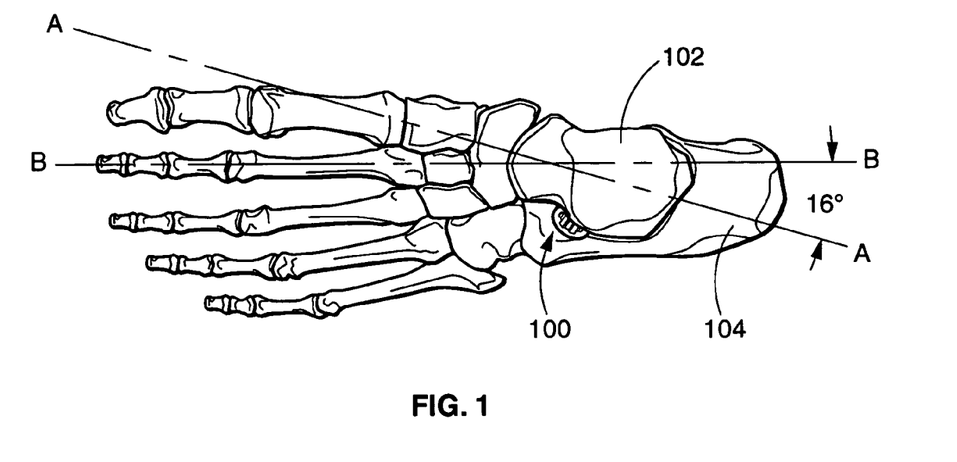
FIG. 1 is a dorsal view of the bone structure of a human foot with a sinus tarsi implant in situ displaying the axis of rotation of the subtalar joint relative to the midline.

Referring now to the drawings wherein like numerals indicate the parts, FIG. 1 is a schematic representation of a patient's foot with a sinus tarsi implant 100 placed in accordance with a preferred embodiment of the invention. As described previously, the implant operates by arthroeresis (blocking of motion) of the patient's subtalar joint. The subtalar joint is the articulation between the talus 102 superiorly and the calcaneus 104 inferiorly. FIG. 1 also illustrates an axis A—A of subtalar joint motion which is approximately 16 degrees measured from a midline axis B—B of a human foot.

Figure 2:
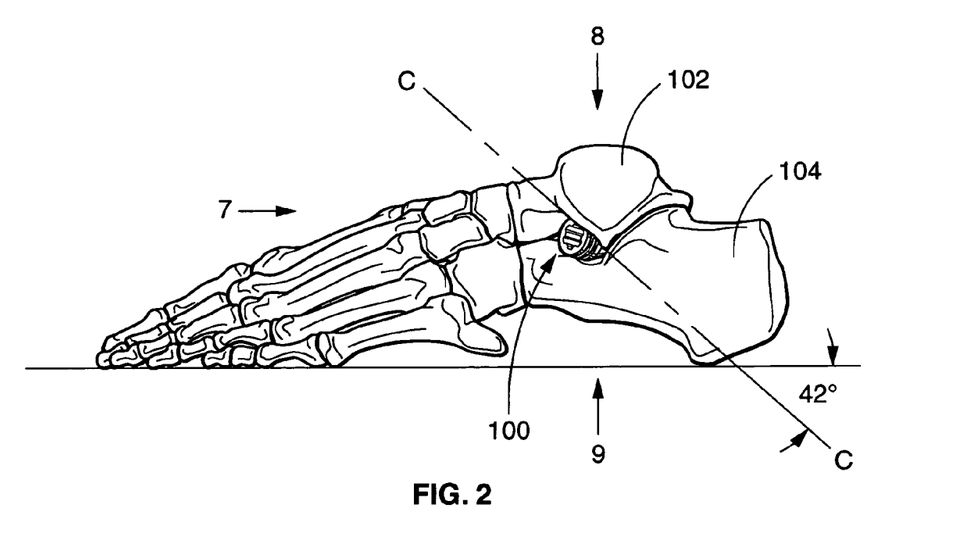
FIG. 2 is a lateral view of the bone structure of a human foot with an implant in situ displaying the axis of rotation of the subtalar joint relative to the horizontal plane.

FIG. 2 depicts the sinus tarsi implant 100, talus 102 and calcaneus 104 in a side view. Also shown, axis C—C of subtalar joint motion is approximately 42 degrees measured with respect to a horizontal plane. FIG. 2 further discloses line-of-sight views "7," "8," and "9" for FIGS. 7–9 respectively.

Figure 3:
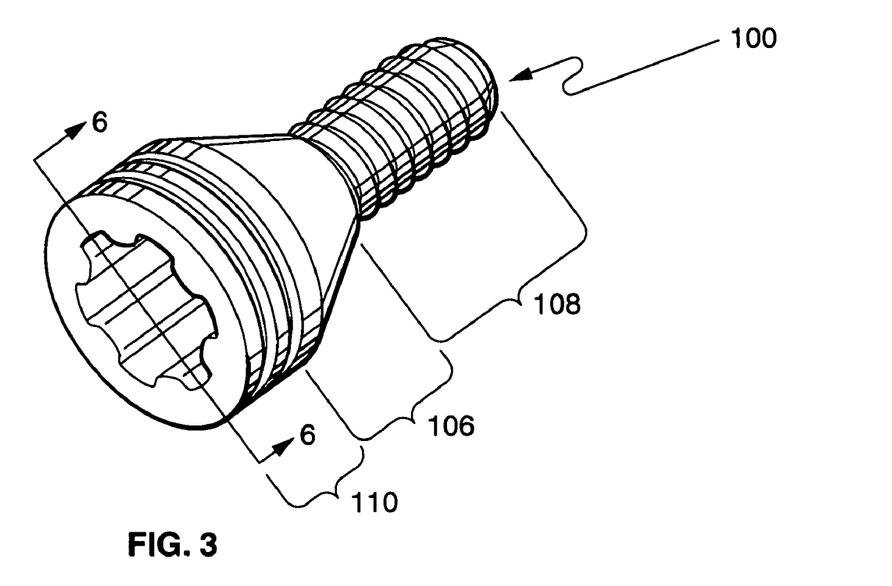
FIG. 3 is a perspective view of a sinus tarsi implant in accordance with a preferred embodiment of the invention.

FIG. 3 illustrates a perspective view of an implant 100 comprising a first member 106 with an outer surface configuration generally in the shape of a frustum of a right cone. A frustum is the portion of a right circular cone lying between a circular cone base and a plane parallel to the base cutting off a top portion of the cone. A second member 108 is longitudinally attached to the frustum member 106 at the smaller end. The second member 108 is preferably a cylinder with a diameter substantially equal to the diameter of the small end of the frustum member 106. FIG. 3 also discloses an optional third member 110 which is another cylindrical member having a diameter substantially equal to the diameter of the base of the frustum 106.

Figure 4:
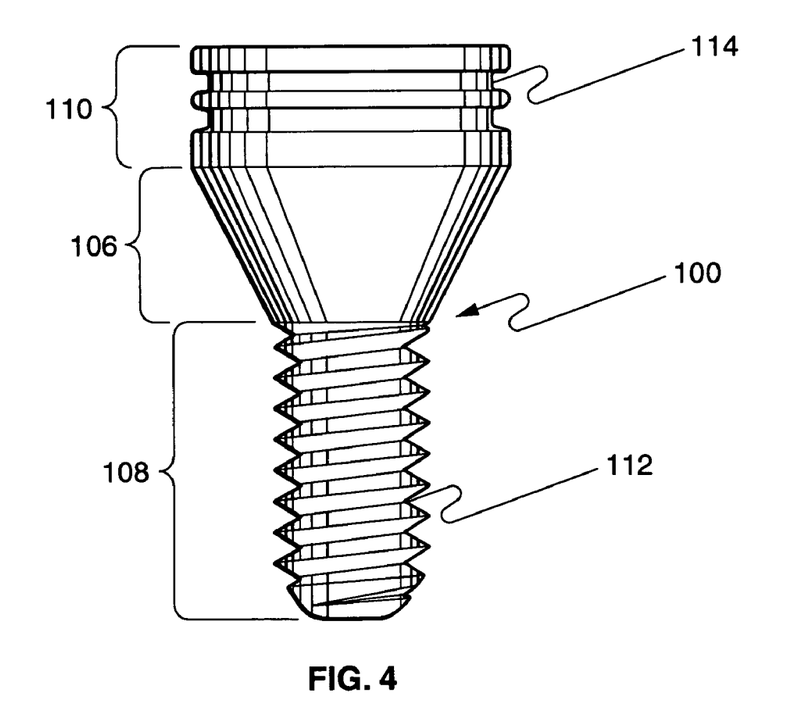
FIG. 4 is a side view of the sinus tarsi implant shown in FIG. 3.

FIG. 4 is a side view of an implant that illustrates the specific members that make up an implant. The size and shape of these members are preferably determined as follows, the first member 106 is designed to sit on the lateral most aspect of the canalis tarsi. (The beginning or outermost aspect of the canalis tarsi. See FIGS. 7–9 described below.) In a preferred embodiment, the first member has an outer surface generally shaped as a right conical frustum. The smaller end is equal in diameter to the second member 108 and the larger end is equal in diameter to the optional third member 110. Together, these members preferably form a continuous solid outer surface. As described below, the first member 106 will also play a role in the correct positioning of the implant.

The second member 108 has an outer surface generally cylindrical in shape with an outer diameter approximately equal to that of the smaller end of the first (or frustum) member 106. Preferably fashioned about the outer surface of the second member is a series of one or more channels 112. In a preferred embodiment, the channeled surfaces are fashioned as a continuous thread. In addition, however, other tissue engagement surfaces are envisioned such as sinusoidal shapes or microporous cylindrical surfaces to promote interactions with connective tissue within the sinus tarsi. The second member 108 is designed to insert into the narrow, medial, portion of the sinus tarsi, the canalis tarsi. Note again FIGS. 7–9 below.

The second member provides the important functions of anchoring the implant 100 in place and preventing collapse of the canalis tarsi canal. The channeling or threading serves to operably engage the surrounding soft tissue and ligaments and thus firmly and permanently anchors the implant in place.

Anchoring the implant with channeling or threading is a significant improvement of prior art methods of anchoring. For example, other subtalar blocking implants were anchored by drilling a vertical hole in the dorsal aspect of the calcaneus that forms the floor of the sinus/outer portion of the sinus tarsi. This lead to a problem of weakening and fracture of the calcaneus.

The outer diameter of the second member 108 is selected to be large enough to prevent collapse of the canalis tarsi canal but not so large as to interfere with normal foot motion. In a preferred embodiment, a set of implants are provided having second member outer diameters ranging 0.6 cm to 1.1 cm in 0.10 cm increments. For this particular embodiment, the proper size is determined as explained below in Surgical Procedures and Instrumentation.

An optional third member 110 is contemplated that extends out from the larger end of the first (or frustum) member 106 in the general shape of a cylinder. In other words, a cylindrical member 110 is axially connected to the base of the frustum 106. This portion of the implant is designed to rest in the outer most (lateral) region of implantation, sitting in the sinus portion of the sinus tarsi, note particularly FIG. 8.

For further stabilization, the outer surface of member 110 can be modified to incorporate tissue engagement surfaces as described above. In a preferred embodiment, one or more peripheral channels 114 are fashioned into the outer surface of member 110 to permit fibrous tissue ingrowth. In a further embodiment, a plurality of two or more peripheral channels can be so fashioned.

The third member 110 is generally not tapered. It has approximately the same outer diameter along its entire length as the base of the frustum 106. However, the third member can also have an outer surface with a slight degree of taper with the slightly larger diameter at the outermost aspect of the implant.

The third member 110 functions (together with the first member) to block medial and anterior deviation of the talus. As a result, the implant blocks hyperpronation of the user's foot while at the same time allowing normal flexing of the user's foot.

In order to properly block abnormal motion while allow normal motion, the third member 110 must have a carefully chosen outer diameter. In a preferred embodiment, a set of implants are provided having third member outer diameters ranging from 0.85 cm to 1.6 cm in 0.15 cm increments.

Figure 5:
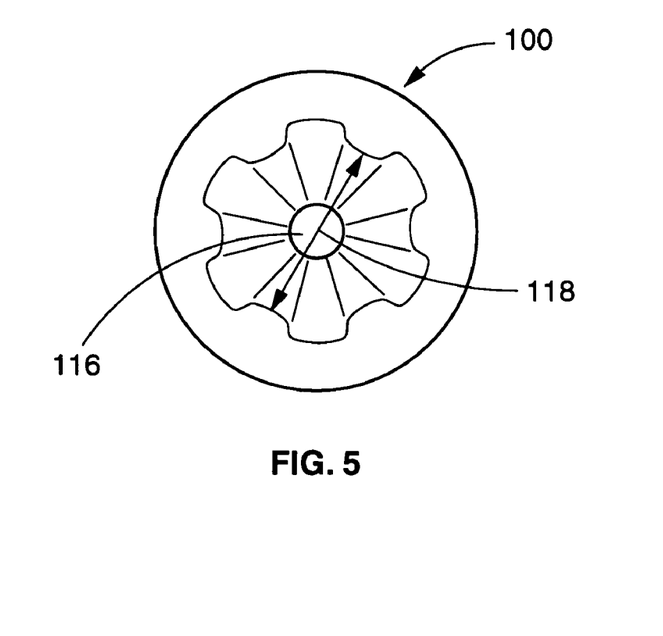
FIG. 5 is an end view of the sinus tarsi implant shown in FIG. 3.

FIG. 5 illustrates a lateral end view of an implant. The lateral end is located at the frustum member base. Alternatively, if an optional third member is attached, the lateral end is at the free end of the third member. In a preferred embodiment, this end is provided with a recess having a selected geometric shape. FIG. 5 illustrates a TORX shaped drive recess 118. The recess is configured to accept the end of an insertion tool having a complementary geometric shape. Preferably, the tool would be inserted into the recess and used to advance the implant into position as explained below. Any geometric shape can be used, preferably a shape in which maximum torque can be applied without slippage. Examples, of suitable shapes include straight slots (flat heads), cruciate (PHILLIPS heads), hexagonal, POSIDRIVE, TORX, Allen-type and others.

Figure 6:
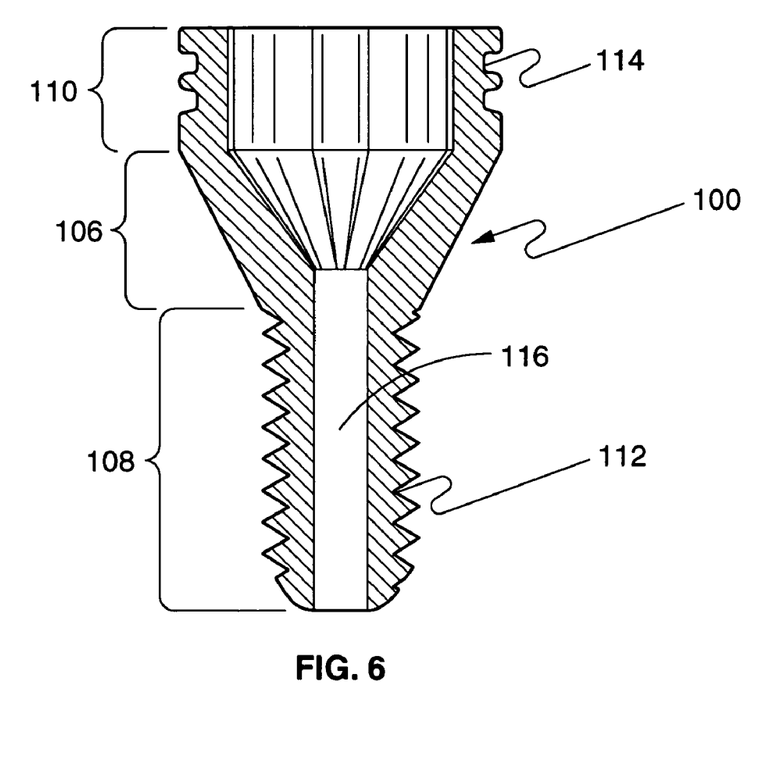
FIG. 6 is a cross-sectional view of the subject sinus tarsi implant taken along section line 6—6 in FIG. 3.

FIG. 6 is a cross-sectional view of a preferred embodiment of the implant. FIG. 6 reveals a cannula or longitudinal bore 116 traversing the entire length of the implant along a central longitudinal axis. The bore is fashioned to allow placement of the implant on a guide to facilitate proper surgical implantation. The implantation method is described below.

Figure 7:
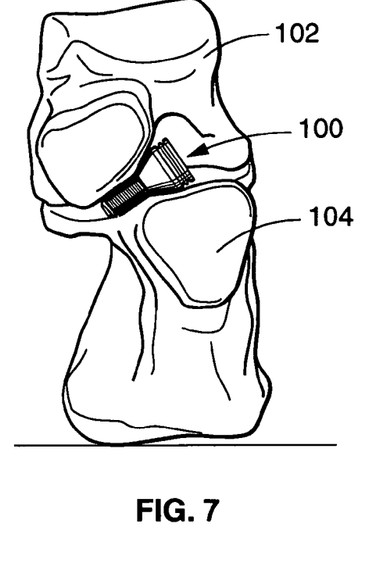
FIG. 7 is a broken away view taken in the general direction of arrow "7" in FIG. 2, of a left foot with a sinus tarsi implant in situ.

Turning now to FIG. 7, note sheet 4, this figure illustrates a left foot viewed from the front generally along line-of-sight "7" in FIG. 2. An implant 100 is shown together with cross-sections of both a left talus 102 and a left calcaneus 104. As explained previously, the implant is properly positioned when the frustum member abuts the lateral most aspect of the canalis tarsi. This can be seen in FIG. 7. The lateral most aspect of the canalis tarsi is the region in which the canal narrows. FIG. 7 illustrates that in the narrowing region an implant is in contact with the surrounding bone.

FIG. 7 also illustrates the second member in the deepest, or medial, end of the canal. The end of the second member is shown abutting the sulcus tali as explained above. Another method by which one insures proper positioning is to insert an implant until the end of the second member abuts the sulcus tali. This method can be used separately or together with the method above.

Figure 8:
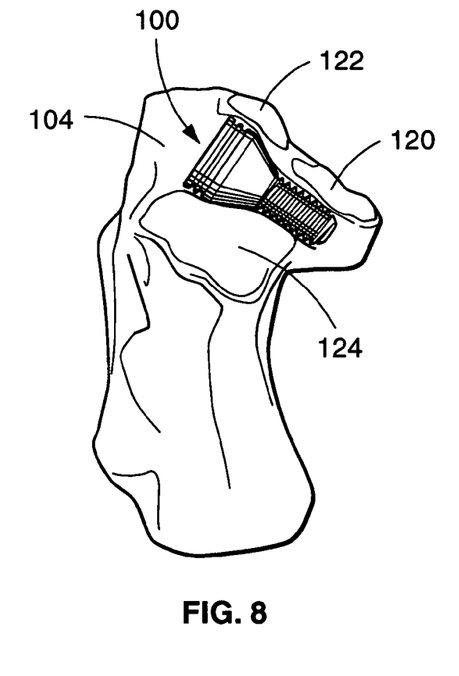
FIG. 8 is a broken away view taken in the general direction of arrow "8" in FIG. 2, of a left foot with the talus removed to reveal the bottom half of the sinus tarsi and an implant in situ in accordance with the subject invention.

FIG. 8 illustrates in detail an implant 100 in situ viewed from above, generally along line-of-sight "8" in FIG. 2. Revealed are the structures of the calcaneus 104 that define the bottom half of the sinus tarsi. The sinus tarsi is posterior to (behind) the talocalcaneonavicular joint which comprises the middle 120 and anterior talar facet 122 of the calcaneus 104. The sinus tarsi is anterior to (in front of) the subtalar joint which comprises the posterior talar facet 124 of the calcaneus 104.

Figure 9:
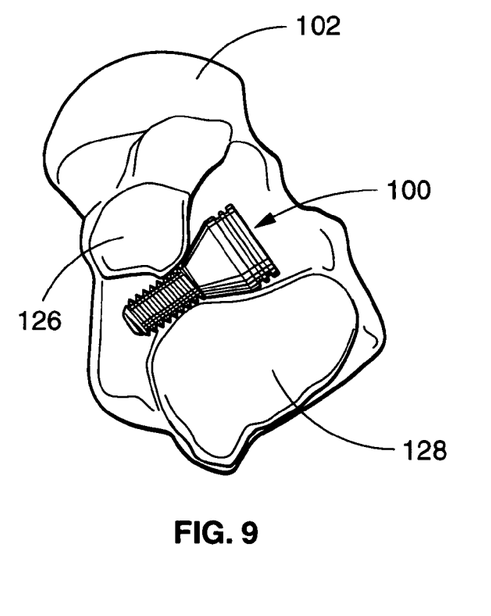
FIG. 9 is a broken away view of taken in the general direction of arrow "9" in FIG. 2, of a left foot with the calcaneus removed to reveal the top half of the sinus tarsi with an implant in situ in a correct anatomical position.

FIG. 9 illustrates an implant 100 in situ viewed from below, generally along line-of-sight "9" in FIG. 2. FIG. 9 reveals the structures of the talus 102 that define the top half of the sinus tarsi. These structures are the complement of those illustrated in FIG. 8. The sinus tarsi is posterior to (behind) the talocalcaneonavicular joint which comprises the middle 126 and anterior calcaneal facet of the talus 102. The sinus tarsi is anterior to (in front of) the subtalar joint which comprises the posterior calcaneal facet 128 of the talus 102.

The subject invention is intended to provide a long term implant with expected useful life ranging from a period of years to a period of decades. Moreover, the subject invention is intended to be operably a permanent implant; one that will rarely or preferably never require replacement over the lifetime of the user. In this, the selected material of an implant 100 must be soft enough so as to prevent excessive wear and deformation of the surrounding bones causing undesirable side effects but, concomitantly, durable enough so that the implant itself will not excessively wear and deform and eventually fail or require premature replacement.

Turning now to the compositions from which the implant is made, in a preferred embodiment, an implant is made entirely from a single substance. The implant composition preferably comprises a medical grade polymer suitable for the insertion in the body in that it is substantially inert with respect to chemical reactions present in the body and is unlikely to result in adverse reactions, infections, adverse immunologic reactions such as allergic reactions or rejection. Still another preferred embodiment is a medical grade polymer suitable for long term or permanent implantation as defined above. It is presently envisioned that the implant composition will comprise suitable polymers such as high molecular weight polyethylene, polyetheretherketone (PEEK), polyetherketoneketone (PEKK), polymethyl-methacrylate (PMMA), polytetrafluoroethylene (PTFE), crystalline plastics, polyoxymethylene and DELRIN.

The implant composition need not be a single substance. Indeed it is envisioned that compositions comprising blends of two or more substances will be suitable. Suitable blends include combinations of polymer fibers dispersed in resins such as DELRIN AF, a blend of PTFE fibers uniformly dispersed in DELRIN acetal resin.

Polymer research has resulted in the development of scores of high grade polymers. These polymers have physical properties that cover the entire range of properties (such as durability and hardness) from metallic and plastic. Accordingly, it is envisioned that many other compositions will be suitable for use with this implant so long as these compositions have the desired properties.

It is also contemplated that multiple substances can be combined to form a hybrid implant combining the advantageous properties of each substance. For example, more durable substances can be combined with more flexible substances. High coefficient of friction substances can be combined with low coefficient of friction substances. These substances can be placed in specific portions of the implant where the corresponding property is most critical. Alternatively, the substances can be blended together in a uniform ratio throughout the entire implant.

Also, while post operative imaging (fluoroscopic, magnetic resonance imaging, etc) is not needed for proper placement of the implant, imaging may be desired for special purposes. In such cases, an opaque structure can be imbedded into the implant or an opaque substance added to the polymer for the purposes of imaging.

It is important to note that in cases where the bone surrounding the implant is protected from wear then harder, more durable materials can be used including metal alloys. For example, biotechnological techniques to stimulate growth of bone cells (osteogenesis) and thus replace worn regions of bone can permit the use of harder materials. Of course, if the implant is only required for a short time then the material from which the implant is made is less critical. Furthermore, any prior art implant material can also be used if the patient is willing to forgo the above advantages of using polymers for any reason.

In the context of this invention, terms such as "generally shaped," "generally configured in the shape," "generally cylindrically configured" etc. are meant to indicate that the implant may, but need not be shaped so as to conform to strict definitions from solid geometry for solids such as "cylinders" and "frustums."

Indeed, in order to provide an implant with the proper size and shape for every patient, a range of sizes and shapes are contemplated. At one extreme, a "standard set" is utilized where a set of "consensus" sizes and shapes implants are pre-manufactured and provided to health care providers and their patients. This particular embodiment has the advantage of being the most uniform and therefore the least expensive for the patient.

At the other extreme, a "custom design" is envisioned where the exact size and shape is determined only after precise, detailed measurements of the inner dimensions of a patient's sinus tarsi. As a result, the generally cylindrical portions of the implant may be tapered or shaped if necessary; however, the general cylindrical configuration will remain. For similar reasons, the first member, or generally frustum shaped portion, may be concave or convex as appropriate; however, the general funnel configuration will remain. In effect, with the custom design method there are as many different shapes and sizes as there are patients. The custom design embodiment has advantages such as the patient receiving a precise amount of arthroeresic correction (degree of blocking of abnormal motion) which could be critical in special cases, for example elite athletes, dancers and others whose occupations place unusual stresses on this region.

Thus, the actual number of different sizes and shapes of implants to be manufactured will ultimately depend upon economic considerations. If cost is the predominant factor than a relatively small number of different sized and shaped implants will be manufactured. On the other hand, as precision fit becomes a more dominant factor, then the number of different sizes and shapes available will increase accordingly, perhaps to a very large number.

In addition to the shape of the implant overall, the shape of the transition between the cylinder and frustum can also vary. This transition need not be abrupt as depicted, for example, in the implant 100 of FIG. 4. (Note the relatively sharp transition edge between the optional third member 110 and the first member 106 and between the first member 106 and the second member 108). Rather, the transition could be smooth and gradual leaving no sharp "edge."

Surgical Procedures and Instrumentation

Instrumentation of this system includes a set of cannulated probing devices, a set of implants, a cannulated insertion tool and a guide wire or guide pin. In a preferred embodiment the probing devices have a diameter ranging from 0.6 cm to 1.1 cm to correspond to the size implant required for correction. Each probing device is increased in diameter by 1 mm.

The sinus tarsi implants are preferably provided in a set that range in size. Measuring from the outer diameter of narrow part of the implant (the second member) the set will, preferable, have a gauge from 0.6 cm to 1.1 cm. Implant size should, preferably, increase 1 mm in diameter from 0.6 cm to 1.1 cm.

A cannulated insertion tool is also included to advance the implant into the sinus tarsi. In a preferred embodiment, the insertion tool functions much like a screw driver as described below.

A preferred operative procedure consists of making a 1 cm to 2 cm linear incision over the sinus tarsi parallel to the relaxed skin tension lines. The incision is deepened via blunt dissection to the sinus tarsi.

The proper angle along which the implant is inserted into the patients sinus tarsi is then determined with one of the probing devices. The 0.6 cm cannulated probing device is inserted into the sinus tarsi from lateral distal dorsal to medial proximal plantar until it is palpated exiting the medial aspect of the sinus tarsi. The angle of the probing device is the proper angle along which the implant is inserted.

A guide (preferably a guide wire or a guide pin) is then inserted into the cannula of the probing device and is left in place until the end of the procedure. Starting with the smallest diameter probe (0.6 cm) subsequent larger sized probes are inserted over the guide until the appropriate size implant is determined.

As noted above, the implant 100 is cannulated (fashioned with a central longitudinal hole or cannula) 116 so that the implant can be placed on the guide followed by the cannulated insertion tool. Through the action of the insertion tool, the implant is then advanced into the sinus tarsi until proper placement is achieved. Correct placement of the implant occurs when the first member 106 abuts the lateral most aspect of the canalis tarsi. (The beginning or outermost aspect of the canalis tarsi.) See the middle members of the implants 100 in FIGS. 7–9. Alternatively, placement can be achieved when the second member 108 abuts the lateral aspect of the talus, the sulcus tali. See the end of the second member (the small member) of implant 100 in FIG. 7.

In a preferred embodiment, the implant is advanced into position by rotation. The implant can be rotated into position by use of any conventional method of applying torque, including the use of manual tools and power tools. In a preferred embodiment, the insertion tool is inserted into a recess on the lateral end of the implant and torque is applied.

After the implant is fully inserted the incision is closed. The method of closure of the incision is surgeon's choice.

Summary of Major Advantages of the Invention

After reading and understanding the foregoing description of preferred embodiments of the invention, in conjunction with the illustrative drawings, it will be appreciated that several distinct advantages of the subject implant system are obtained.

Without attempting to set forth all of the desirable features and advantages of the implant and associated methods, at least some of the major advantages of the invention are the stabilization of both the medial and lateral aspects of the talus and calcaneus by the corresponding segments of the implant in contact with these regions which results in blocking hyperpronation of the foot while allowing normal motion.

Another advantage is the long useful lifetime of the implant. When the implant is made of the correct material, it will neither wear the surrounding bones nor will the implant wear.

A related advantage that also increases the lifetime of the implant is the permanent anchoring of the implant by way of the peripheral channels and threading. Failure due to slippage out of position will be rare or absent. Also, the surrounding bones remain strong as compared to procedures in which anchoring is achieved by drilling a hole into the calcaneus or the use of other invasive anchoring methods. As a result, complications stemming from weak surrounding bones are unlikely.

A still further advantage of the implant system is the ability to accurately position the implant without irradiation. The implant is correctly positioned when the implant abuts the lateral most aspect of the canalis tarsi or the sulcus tali or both. Thus, there is no need for a fluoroscope (and irradiation of the user's foot) to verify the positioning.

Another advantage of the subject sinus tarsi implant is primary correction of hyperpronation, talipes valgus, pes planus, and other related rearfoot and forefoot deformities. The implant will also be used for secondary correction of growing pains, shin splints, posterior tibial tendon dysfunction, plantar fasciitis, hallux abductovalgus, metatarsus primus varus and elevatus, metatarsus adducts, contracted toes, abnormal gait, intermetarsal neuromas, as well as sciatica, patellofemoral pain, genu varum anterior pelvic tilt, lumbar lordosis, etc.

Yet, another advantage is that the implant is inserted via a minimally invasive procedure and no casting is needed following the procedure so that there is a quick recovery.

In describing the invention, reference has been made to preferred embodiments. Those skilled in the art and familiar with the disclosure of the subject invention, however, may recognize additions, deletions, substitutions, modifications and/or other changes which will fall within the purview of the invention as defined in the following claims.

What is claimed is:

1. A method of correcting anatomical alignment of a patient's ankle bone structure comprising:
   inserting an implant into a sinus tarsi of a patient,
   said implant comprising,
      a first member having an outer surface generally configured in the shape of a right conical frustum having a base portion and a top portion, and being inserted into a sinus region of the patient's sinus tarsi;
      a second member, axially connected to the top of said first member and having an outer surface generally configured in the shape of a cylinder and having an outer diameter approximately equal to the top portion of said first member and being inserted into a canalis tarsi region of the patient's sinus tarsi; and
      a third member, axially connected to the base of said first member an having an outer surface generally configured in the shape of a cylinder and being inserted into the sinus region of the patient's sinus tarsi;
   wherein said first, second and third members maintain said sinus tarsi in an anatomically correct alignment and minimize a tendency for abnormal motion between the patent's talus and calcaneus thereby correcting deformities in the patient's ankle bone structure.

2. A method of correcting anatomical alignment of a patient's ankle bone structure as defined in claim 1 wherein said third member further comprises:
   at least one peripheral channel fashioned about said third member outer surface to engage surrounding tissue and permit fibrous tissue ingrowth to anchor said implant within the patient's sinus tarsi.

3. A method of correcting anatomical alignment of a patient's ankle bone structure as defined in claim 1 wherein said second member further comprises:
   a channeled surface fashioned in said second member outer surface to engage surrounding tissue and permit fibrous tissue ingrowth to anchor said second member within the canalis tarsi region of the patient's sinus tarsi.

4. A method of correcting anatomical alignment of a patient's ankle bone structure as defined in claim 3 wherein said channeled surface further comprises:
   a continuous thread fashioned in said second member outer surface to engage surrounding tissue and permit fibrous tissue ingrowth to anchor said second member within the canalis tarsi region of the patient's sinus tarsi.

5. A method of correcting anatomical alignment of a patient's ankle bone structure as defined in claim 4 wherein said implant further comprises:
   a recess fashioned within a lateral end of said implant and being configured to accept a tool so that when the tool is inserted into the recess the tool is operable to advance the implant into a proper position.

6. A method of correcting anatomical alignment of a patient's ankle bone structure as defined in claim 1 wherein said sinus tarsi implant is composed of a composition comprising:
   a medical grade polymer suitable for implantation in the patient without adverse reactions.

7. A method of correcting anatomical alignment of a patient's ankle bone structure as defined in claim 1 wherein said sinus tarsi implant is composed of a composition comprising:
   a polymer selected from the group consisting of high molecular weight polyethylene, polyoxymethylene, DELRIN, polyetheretherketone (PEEK), polyetherketoneketone (PEKK), polymethylmethacrylate (PMMA) polytetrafluoroethylene (PTFE) and DELRIN AF.

8. A method of correcting anatomical alignment of a patient's ankle bone structure as defined in claim 1 and further comprising:
   a longitudinal bore traversing the entire length of the implant along the implant longitudinal central axis and fashioned to allow placement of the implant on a guide to facilitate proper surgical implantation.

9. A method of correcting anatomical alignment of a patient's ankle bone structure as defined in claim 1 and further comprising:
   said second member outer diameter is in a range from 0.6 cm to 1.1 cm.

10. A method of correcting anatomical alignment of a patient's ankle bone structure comprising:
    inserting an implant into a sinus tarsi of a patient,
    said implant comprising,
       a first member having an outer surface generally configured in the shape of a frustum of right cone having a circular base portion and a circular top portion with said top portion diameter less than said base portion diameter, and said first member being inserted into a sinus region of the patient's sinus tarsi,
       a second member, axially connected to the circular top portion of the first member and having an outer surface generally configured in the shape of a cylinder and having an outer diameter approximately equal to the diameter of the top portion of said first member and being inserted into a canalis tarsi region of the patient's sinus tarsi, and
       a third member axially connected to said base portion of said first member, said third member having an outer surface generally configured in the shape of a cylinder with an outer diameter approximately equal to the diameter of the base portion of said first member and being inserted into a sinus region of the patient's sinus tarsi,
    wherein said implanted members maintain said sinus tarsi in an anatomically correct alignment and minimize a tendency for abnormal motion between the patent's talus and calcaneus in the patient's ankle bone structure.

11. A method of correcting anatomical alignment of a patient's ankle bone structure as defined in claim 10 wherein said third member further comprises:
    at least one peripheral channel fashioned about said third member outer surface to engage surrounding tissue and permit fibrous tissue ingrowth to anchor said implant within the patient's sinus tarsi.

12. A method of correcting anatomical alignment of a patient's ankle bone structure as defined in claim 11 wherein said at least one peripheral channel further comprises:
    at least a first and a second peripheral channel being axially spaced along the outer surface of said third member to engage surrounding tissue and permit fibrous tissue ingrowth to anchor said implant within the patient's sinus tarsi.

13. A method of correcting anatomical alignment of a patient's ankle bone structure as defined in claim 10 wherein said second member further comprises:
    a channeled surface fashioned in said second member outer surface to engage surrounding tissue and permit fibrous tissue ingrowth to anchor said second member within the canalis tarsi region of the patient's sinus tarsi.

14. A method of correcting anatomical alignment of a patient's ankle bone structure as defined in claim 13 wherein said channeled surface further comprises:
    a continuous thread fashioned in said second member outer surface to engage surrounding tissue and permit fibrous tissue ingrowth to anchor said second member within the canalis tarsi region of the patient's sinus tarsi.

15. A method of correcting anatomical alignment of a patient's ankle bone structure as defined in claim 14 wherein said implant further comprises:
    a lateral end fashioned with a recess configured to accept a tool so that when the tool is inserted into the recess the tool is operable to advance the implant into a proper position.

16. A method of correcting anatomical alignment of a patient's ankle bone structure as defined in claim 10 wherein said sinus tarsi implant is composed of a composition comprising;
    a medical grade polymer suitable for implantation in the patient without adverse reactions.

17. A method of correcting anatomical alignment of a patient's ankle bone structure as defined in claim 10 wherein said sinus tarsi implant is composed of a composition comprising:
    a polymer selected from the group consisting of high molecular weight polyethylene, polyoxymethylene, DELRIN, polyetheretherketone (PEEK), polyetherketoneketone (PEKK), polymethylmethacrylate (PMMA) polytetrafluoroethylene (PTFE) and DELRIN AF.

18. A method of correcting anatomical alignment of a patient's ankle bone structure as defined in claim 10 wherein said implant further comprises:
    a longitudinal bore traversing the entire length of the implant along a central longitudinal axis and fashioned to allow placement of the implant on a guide to facilitate proper surgical implantation.

19. A method of correcting anatomical alignment of a patient's ankle bone structure as defined in claim 10 and further comprising:
    said second member outer diameter is in a range from 0.6 cm to 1.1 cm.

* * * * *